United States Patent
Aleksandrovskiy et al.

(10) Patent No.: US 7,677,892 B2
(45) Date of Patent: Mar. 16, 2010

(54) METHOD AND EXTRACTOR FOR REMOVING A TOOL FRAGMENT FROM A TOOTH ROOT CANAL

(76) Inventors: Vladimir Leonidovich Aleksandrovskiy, Kosmodamianovskaya nab., #28/30-8, Apt. 25, Moscow (RU) 113035; Alexander Borisovich Tsyganov, ul. Nalichnaya, #45, bldg. 1, apt. 5, St. Petersburg (RU) 199397

( * ) Notice: Subject to any disclaimer, the term of this patent is extended or adjusted under 35 U.S.C. 154(b) by 96 days.

(21) Appl. No.: 11/464,350

(22) Filed: Aug. 14, 2006

(65) Prior Publication Data

US 2006/0286511 A1    Dec. 21, 2006

Related U.S. Application Data

(63) Continuation of application No. PCT/RU2005/000052, filed on Feb. 10, 2005.

(30) Foreign Application Priority Data

Feb. 13, 2004    (RU) .............................. 2004104003

(51) Int. Cl.
*A61C 5/02* (2006.01)
*A61C 3/00* (2006.01)
(52) U.S. Cl. .......................... 433/224; 433/32; 433/141
(58) Field of Classification Search ................. 433/141, 433/224, 215, 220, 152, 32; 219/55, 86.1
See application file for complete search history.

(56) References Cited

U.S. PATENT DOCUMENTS 3,322,124 A * 5/1967 Ireland ........................ 433/141

(Continued)

FOREIGN PATENT DOCUMENTS

RU    2239463 C1    11/2004

(Continued)

OTHER PUBLICATIONS

International Search Report from International application No. PCT/RU2005/000052, filed Feb. 10, 2005, mailed Jun. 16, 2005.

(Continued)

*Primary Examiner*—John J Wilson
(74) *Attorney, Agent, or Firm*—Houston Eliseeva LLP

(57) ABSTRACT

The method and extractor relate to dentistry and are intended for extraction of metal instruments fragments from a root canal of the tooth, as these instruments may be broken and may get stuck here, for example, during endodontic treatment. According to the invention, two insulated metal electrodes assembled as a cylinder are inserted into the root canal until electric contact with the fragment to be extracted. Then electric current impulse is ran through the circuit formed by the first electrode, metal fragment and second electrode; the intensity and duration of the electric impulse shall be sufficient for welding of the fragment to the electrodes by means of heating at the contact points; this time a heating of the surrounding tissues remains at the physiologically acceptable level; afterwards the electrodes are extracted from the root canal together with the fragment. Depending on a clinical situation, electrodes of various size and configuration are used. Electric impulse is generated by the unit comprising a capacitor chargeable by a battery and dischargeable in pulsed mode via controlled electronic switch. The unit also has an indicator of contact resistance between the fragment and the electrodes for a better alignment of their relative positions.

5 Claims, 5 Drawing Sheets

U.S. PATENT DOCUMENTS

| | | | |
|---|---|---|---|
| 3,899,653 A * | 8/1975 | Spinnato | 219/113 |
| 4,337,038 A | 6/1982 | Saito et al. | |
| 4,746,292 A | 5/1988 | Johnson | |
| 4,992,045 A * | 2/1991 | Beisel | 433/32 |
| 5,097,100 A * | 3/1992 | Jackson | 174/94 R |
| 5,879,160 A | 3/1999 | Ruddle | |
| 6,227,855 B1 | 5/2001 | Hickok et al. | |
| 2003/0124485 A1 | 7/2003 | Teraushi | |

FOREIGN PATENT DOCUMENTS

| | | |
|---|---|---|
| SU | 331591 | 1/1974 |
| SU | 1809760 A3 | 4/1993 |

OTHER PUBLICATIONS

English translation of abstract of Soviet Union Patent No. SU 331591, issued Jan. 10, 1974.

English translation of abstract of Soviet Union Patent No. SU 1809760, issued Apr. 15, 1993.

\* cited by examiner

METHOD AND EXTRACTOR FOR REMOVING A TOOL FRAGMENT FROM A TOOTH ROOT CANAL

RELATED APPLICATIONS

This application is a Continuation of PCT application serial number PCT/RU2005/000052 filed on Feb. 10, 2005, published as WO 2005/077286 A1 on Aug. 25, 2005, which claims priority to Russian application serial number 2004104003 filed on Feb. 13, 2004, and both of which are incorporated herein by reference in their entirety.

FIELD OF THE INVENTION

The present invention relates to dentistry and is intended for extraction of the fragments of the metal tools, which may be broken and may get stuck in the root canal of the tooth, for example, during endodontic treatment.

BACKGROUND OF THE INVENTION

There are known several devices used for extraction of the tool fragments from the root canal of the tooth (U.S. Pat. No. 5,879,160 and U.S. Pat. No. 6,227,855) by means of the mechanical clamp introduced into the canal through the cylindrical tube and ensuring grasping of the fragment. When this technique is used, the clamp is removed from the canal together with the tube and the grasped fragment. A common feature being peculiar both to the present invention and to the aforesaid prior art devices is insertion of the tool into the root canal until it comes in contact with the fragment and extraction of the tool together with the grasped fragment.

However, application of said devices requires undesirable expansion of the root canal up to the stuck fragment, since the fragment should be grasped with the clamp. It is also difficult to control the contact and grasping of the fragment with the tool due to limited access into the narrow root canal (diameter of its opening is about 0.2-1 mm). Besides, since the root canal is often curved, it is rather difficult to transmit mechanical force to the clamp sufficient for reliable grasping of the fragment. Therefore, it is often not possible to reach necessary gripping cohesion between the tool and the fragment stuck in the root canal with certain friction and it can not be removed.

It is known device (US patent application No. 20030124485) similar in its operating principle and used for extraction of the tool fragments from the root canal of the tooth by means of the wire loop introduced into the canal via the cylindrical tube and ensuring grasping of the fragment. However, application of the said device also implies undesirable expansion of the root canal up to the struck fragment. Moreover, it is difficult to attain the necessary gripping between the wire loop and metal fragment of random shape, when the clamping is not controlled.

It is known another device for the extraction of the tool fragments from the root canal of the tooth (U.S. Pat. No. 4,746,292) by means of adhesive introduced into the canal via the cylindrical tube and ensuring adhesion of the fragment to the tube for subsequent extraction. Common feature being peculiar both to the present invention and to said device is introduction of the tool into the root canal until it comes in contact with the fragment and extraction of the tool together with the grasped fragment. However, application of said device requires undesirable expansion of the root canal up to the stuck fragment so that the cylindrical tube could envelop the fragment. Besides, self-hardening adhesive attains required strength rather slowly. Therefore, the patient has to stay in the dental chair experiencing further inconvenience. Moreover, due to the random shape of the fragment and its loose grasping by the cylindrical tube the adhesive may leak into the root canal leading to unacceptable adhesion of the cylindrical tube to the canal walls.

U.S. Pat. No. 4,337,038 is most closely related to the present invention in the entire combination of features and is chosen as the nearest analog. It describes the method and the device for extraction of the tool fragments from the root canal of the tooth by means of electrolytic dissolution of this metal fragment. According to this nearest analog, the first insulated metal electrode in form of cylindrical tube is introduced into the root canal of the tooth stopping short before the metal fragment. Additionally, the second insulated electrode shaped as a needle is also used. It comes through said cylindrical tube and is moved until electric contact with the metal fragment. Physiologically compatible electrolyte is fed into the gap between the fragment and the cylindrical tube. Electropositive potential is applied to the needle electrode and electric current of the physiologically acceptable rate is furnished to the aforementioned electrodes until the fragment is dissolved as a result of the electrolysis.

Common features of the nearest analog and present invention are as follows: at least two insulated metal electrodes are introduced into the root canal until electric contact between one electrode and metal fragment to be extracted, then electric current is applied to the electrodes. However, according to nearest prior art significant current shall be applied to the electrodes for a long period of time, so that to dissolve the metal fragment. As a result, the patient experiences inconveniences. Moreover, due to their high mobility in the solution the dissolved metal cations constituting the fragment and electrolytic anions will be diffused in the surrounding wet tooth tissues, which, as is known, have numerous pores. It may lead to undesirable toxic aftereffects.

SUMMARY OF THE INVENTION

The present invention is aimed to develop method and device for a fast and reliable extraction of the fragments of the metal instruments, which may be broken and may get stuck in root canal of the tooth, for example, during endodontic treatment. Instruments for endodontic treatment, as a rule, are made from steel or Ni—Ti alloys and have a conic shape with a sharp end and cutting tips located throughout the length of the instrument for root canal processing and removal of infected dentine.

The instrument sets of certain range of sizes are used for treatment of the root canals of different shapes and diameters. Diameter of the thickest part of the tools are usually about 1 mm. Diameter of the tip section at 5 mm away from the end is about 0.2-0.3 mm. Unfortunately, in the course of mechanical treatment of the root canal of the tooth these instruments can suffer sudden breakage and their fragments get stuck in the root canal. If the fragment is not extracted, it is impossible to complete endodontic treatment of the tooth with removal of the infected tooth tissues and filling of the root canal in, e.g. with gutta-percha. So, a failure in fragment extraction may lead to clinical complications. To reach said aim, the nearest analog method for extraction of the metal fragment from the root canal of the tooth, where at least two insulated metal electrodes are introduced into the root canal up to electric contact between one electrode and metal fragment to be extracted; then electric current is applied to electrodes, have been modified, as follows.

According to the present invention, introduced into the root canal insulated electrodes have a shape which shall ensure simultaneous electric contact of both electrodes with the metal fragment. Further, electric pulsed current is applied at the closed circuit formed by the first electrode, metal fragment and second electrode, the current value and duration of the electric pulse shall be sufficient for attachment of the fragment to the electrodes by means of heating of the contact points; afterwards the electrodes are extracted from the root canal together with the fragment. As a rule, additional expansion of the root canal can be avoided, since said insulated electrodes can be made as a cylindrical assembly with the end diameter similar to the diameter of the root canal opening near the fragment. Therefore, the electrodes can be easily introduced into the root canal until they come into "butt end-to-butt end" contact with the fragment. Duration of said electric pulse necessary for attachment of the fragment to the electrodes via heating in the contact points can constitute several fractions of a second unlike the nearest analog prior art, where a considerable time is required for dissolution of the fragment by electrolysis. Retaining strength between the fragment and electrodes will also be sufficient for extraction of the electrodes together with the fragment due to local contact micro-welding during the heating. Unlike the nearest analog prior art, the material of the fragment is not diffused into the tooth tissues, as the fragment is extracted as a whole. So, the metal fragment of the instrument can be extracted quickly and efficiently.

According to another preferred embodiment of the present invention, physiologically compatible chemical agent reducing the clamping force of the instrument fragment in the root canal is introduced before electrodes insertion into the root canal. It facilitates extraction of the fragment, if at the first attempt the retaining strength between the fragment and the electrodes was insufficient and the fragment was detached from the electrodes during their extraction from the canal.

According to another preferred embodiment of the present invention, ultrasonic waves of the physiologically acceptable intensity reducing the clamping force ("loosening") of the instrument fragment inside of the root canal can be applied to the cylindrical element introduced into the root canal in touch to the fragment before the electrodes insertion. It also facilitates extraction of the fragment, if at the first attempt the retaining strength between the fragment and the electrodes was insufficient and the fragment was detached from the electrodes during their extraction from the canal.

According to another preferred embodiment of the present invention, value and duration of the electric current is controlled to achieve optimal attachment of the fragment to the electrodes with a minimal heat impact on the surrounding tooth tissues, i.e. current value shall depend on contact resistance between the fragment and electrodes and the current shall be disrupted, when the contact resistance reaches pre-determined value confirming attachment of the fragment to the electrodes.

Also, to reach said aim, the nearest analog device for extraction of the metal fragment from the root canal of the tooth, comprising electric power supply source and two connected insulated metal electrodes with cross section permitting their simultaneous introduction into the root canal where one of them contacts metal fragment, have been modified, as follows. According to the present invention, aforesaid electrodes have configuration which allows reaching electrical contact between said metal fragment and each of electrodes introduced into the root canal. Additionally, current supply source is made to provide electric current impulse through the closed circuit formed by the first electrode, metal fragment and second electrode sufficient for attachment of the fragment to the electrodes due to heating at the contact points. Unlike the nearest prior art analog, electric current is used only for attachment of the fragment to the electrodes, but not for a complete dissolution of the fragment.

According to another preferred embodiment of the present invention, said insulated electrodes are assembled in cylindrical configuration, while each electrode has a form of semicylinder; these semicylinders are bound to each other by their flat surfaces with dielectric lengthwise between; butt-end of the electrodes contacting the fragment have no dielectric material. Configuration of these two electrodes may vary. However, from the point of view of easy fabrication, breaking strength, minimization of electric resistance of the electrodes and, therefore, voltage applied to electrodes, the best configuration is two semi-cylindrical electrodes having equal cross section throughout the length.

According to another preferred embodiment of the present invention, the butt-end surface of said insulated electrodes is flat to make a contact with a flat butt-end fragment. It provides maximum possible contact area between the electrodes and the flat fragment.

According to another preferred embodiment of the present invention, the butt-end of the insulated electrodes can be concave. It facilitates contact between the introduced electrode and the convex fragment and ensures maximum possible contact area between the electrodes and the convex fragments, among them fragments with random notches.

According to another preferred embodiment of the present invention, cylindrical assembly of the insulated electrodes has end tapering similar in configuration to the root canal in vicinity of the contact area with the fragment. It ensures minimal total electrical resistance of the electrodes, since the root canal is usually of cone shape, and automatically allows in-line arrangement and maximum contact between the fragment and the electrodes.

According to another preferred embodiment of the present invention, the electrodes in the cylindrical assembly are coated with the polymer dielectric material, with the exception of the butt-end faces. This dielectric coating on the surface of the cylindrical assembly provides additional fastening of the electrodes to each other and limits the current flow only in the area of the fragment.

Also, according to another preferred embodiment of the present invention, teflon can be used as said polymer dielectric material. This polymer is characterized by the highest temperature resistance as well as good dielectric and mechanical properties.

In compliance with another preferred embodiment of the present invention, said electrodes are made from material identical to the material of said fragment of metal instrument. It provides the same heating conditions for the contact areas of said electrodes and said fragment by the electric current as well as optimal conditions for their contact micro-welding and solid mutual attachment.

According to another preferred embodiment of the present invention, said metal electrodes beyond of the area of possible contact with the fragment are coated with the material having specific electrical resistance less than the latter of the electrode. It provides reduction of electric voltage applied for a pre-determined current value, as it is enough to coat a thin layer of more conductive material for a considerable reduction of the total resistance of the electrodes without increase in the cross section of the assembly.

In compliance with another preferred embodiments of the present invention, copper, silver or gold can be used as said material with a high electrical conductivity.

According to another preferred embodiment of the present invention, said source of electric current is made on the basis of a capacitor which is charged with a pre-determined voltage value by a power supply unit and then is discharged by a controlled pulsed switch via said electrodes and said fragment. It provides to generate an electric current impulse of necessary value and duration, when powered, among others, from an accumulator battery without a plug in electric mains.

In compliance with another preferred embodiment of the present invention, current supply source may be designed with an indication of contact presence and of electric resistance value between said electrodes and metal fragment; it may be designed also to generate said current impulse on command. It ensures control of the process of introduction of the electrodes into the root canal until they contact the fragment, finding of the best relative position of the electrodes and the fragment for contact micro-welding and following said micro-welding on the dentist's command.

According to the other preferred embodiments of the present invention, current supply source may be designed to maintain a stable voltage or current value in the circuit including said electrodes and said metal fragment, in order to attain the optimal strength of the contact microwelding of the fragment to the electrodes and to disconnect timely when optimal attachment strength is achieved. In some cases it ensures the best attachment of the fragment to the electrodes and its reliable extraction.

BRIEF DESCRIPTION OF THE DRAWINGS

FIG. 2-a is a cross section view of the aforementioned assembly.

FIG. 3-a is a cross section view of the aforementioned assembly.

FIG. 4-a is a cross section view of the aforementioned assembly.

DETAILED DESCRIPTION OF THE PREFERRED EMBODIMENTS

Figure 1:
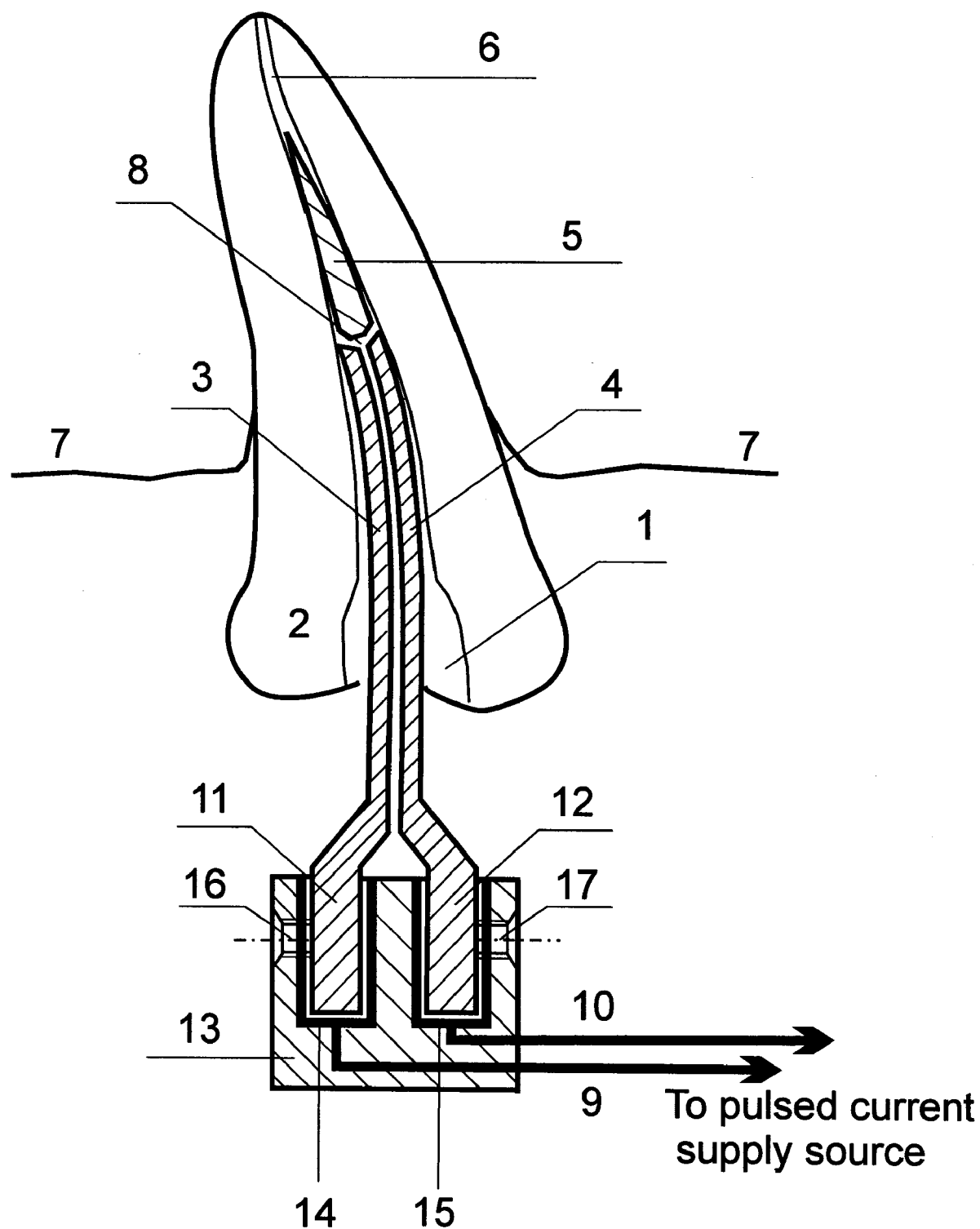
FIG. 1 depicts a tooth diagram and relative position of instrument fragment located inside a root canal and of two insulated electrodes used for its extraction.

The method suggested for extraction of a metal instrument fragment from the tooth root canal is explained in FIG. 1. It comprises an introduction through the entry 1 into the root canal of the tooth 2 of two insulated electrodes 3 and 4 until they contact instrument fragment 5, which got stuck, for example, in the apical (upper) section 6 of the root canal. Then electric current impulse is furnished to the circuit formed, in series, by the electrode 3, fragment 5 and electrode 4 providing a micro-welding of the fragment 5 to the electrodes 3, 4 due to a local heating at contacting points. Afterwards, the electrodes 3, 4 are extracted from the tooth 2 together with attached fragment 5. The level of gum near the tooth is shown schematically by the line 7. Position of the instrument fragment 5 in the apical section of the root canal 6, as well as, in some cases, its configuration face in the direction to entry 1 of the root canal are determined in the course of a radiographic examination. It provides a criterion for selection of the electrodes 3, 4 of the relevant configuration and size. When electrodes 3, 4 are introduced into the root canal 6, an alteration of electric resistance in the circuit indicates about the contact between the electrodes 3, 4 and the fragment 5.

It is common knowledge that a heat power P released during electric current flow through a selected section of the circuit equals:

$$P = I^2 \cdot R \qquad (1)$$

where I—is current value in the circuit;
R—is resistance of the circuit section.

When an electric impulse flows, the current value throughout the circuit is uniform. Therefore, the energy is mainly released in the area 8, where the electrodes 3, 4 contact the fragment 5, as the contact resistance has the greatest value in this circuit and which considerably exceeds the resistance of the electrodes 3, 4 and supply wires 9, 10 of the current supply source (the source is not depicted on FIG. 1 to simplify the drawing). It results in exclusively local heating of contact area 8 between electrodes 3, 4 and the fragment 5, while the electrodes 3, 4 and supply wires 9, 10 get heated only to a minor extent. Herewith, the voltage applied to the electrodes from the pulsed current supply source remains at physiologically acceptable level (less 12V) and is applied mainly to the area of the fragment 5 located in the root canal 6 of the tooth 2 outside the patient's soft tissues. Said impulse is also run for a rather short period of time (0.1 seconds or less). In such conditions the butt-ends of the electrode 3, 4 and adjacent metal fragment 5 are heated locally and for a short period of time, which doesn't lead to a temperature rise of the surrounding tissues of the tooth above a physiologically acceptable level.

To improve conditions of attachment of the fragment 5 to the electrode 3, 4 during the pulsed heating and to reduce heat transfer onto the surrounding tissues of the tooth the root canal 1 and 6 may be dried beforehand with common dental means before the run of the electrical impulse. Electrodes 3 and 4 are elongated into contact elements 11 and 12 which are fixed in miniature handle 13 at the contact groups 14 and 15 with the wires 9 and 10 used to connect to the pulsed current supply source. Configuration of the contact elements 11 and 12 can be of various shapes and corresponding to configuration of the contact groups 14 and 15, e.g. cylindrical.

The dentist introduces the electrode 3, 4 via the entry 1 into the root canal of the tooth 2 and extracts them together with the fragment 5 holding the handle 13. Therefore, the force retaining the electrodes 3, 4 in the handle 13 shall exceed possible extracting force which may occur during removal of the fragment 5 stuck in the root canal 6. Design of the contact groups 14 and 15 in the handle 13 shall also provide for reasonably quick replacement of the electrodes 3, 4 suitable for a selection of the electrode size depending on the canal diameter and size of the fragment. That's why the contact elements 11 and 12 of the electrodes 3, 4 can be fixed in the contact groups 14 and 15 of the handle 13 by means of the screws 16 and 17 or by means of collet clamps. It is also expedient to install the supply wires 9 and 10 in such a way, so that they were coming out of the handle 13 at the right angle to the electrodes 3, 4. It will reduce the overall length of the handle 13 and will facilitate access to posterior teeth (molars) in the patient's mouth.

If the tool fragment 5 got stuck in the root canal 6 with considerable force and the first attempt of its extraction failed, a physiologically compatible chemical agent reducing the clamping force of the instrument fragment inside the root canal may be introduced into the root canal 6 prior to the second attempt. Sodium hypochlorite and/or the agent for a chemical expansion of the canal (for example, with ethylenediaminetetraacetic acid) partially dissolving and softening the root dentin around the fragment 5 can be used. Also a tip of the ultrasonic wave source having physiologically acceptable intensity can be introduced into the root canal 6 till a touch with the fragment 5, so that it could loosening the instrument fragment 5 inside the root canal 6 and reducing its clamping force.

Figure 2:
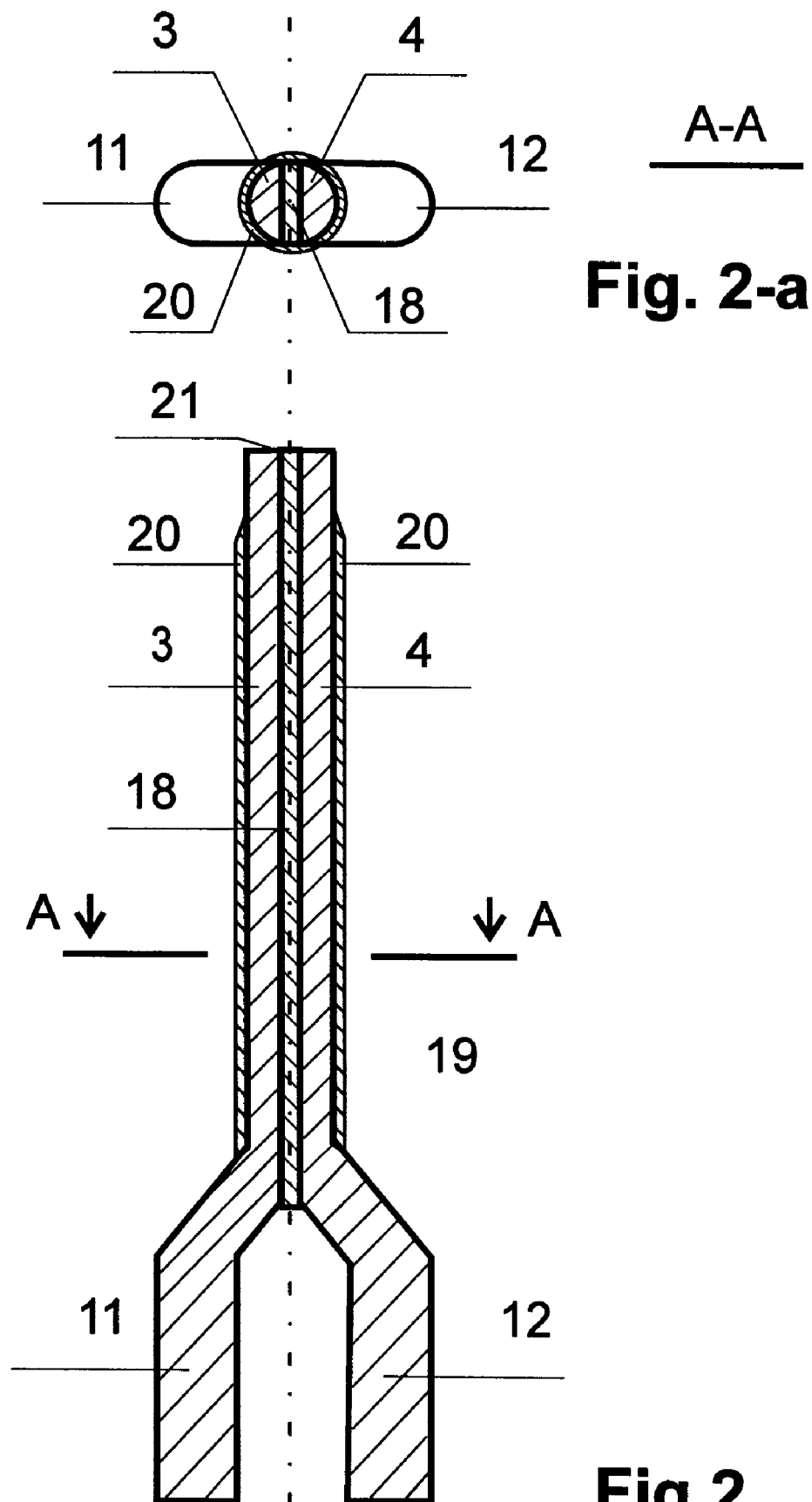
FIG. 2 is a drawing of a cylindrical assembly of insulated electrodes used for extraction of the instrument fragment from the root canal with flat butt-ends.

Although the configuration of the electrodes 3, 4 can be rather random, with regard to the electrical parameters it is expedient that their cross sections and therefore electrical conductivity be equally maximal. In particular, a coaxial design of the electrodes 3, 4 is possible, but in this case a simultaneous contact between the electrodes 3, 4 and the fragment 5 having, for example, a protrusion close to the axis can not be sometimes reached. Thereby, it may be a contact with the inner coaxial electrode, but a contact with the outer coaxial electrode may be absent. The preferred configuration of that part of the electrodes, which is introduced into the canal, is shown in FIG. 2. Hence, the electrodes 3, 4 have a shape of semicylinders with a layer of dielectric 18 in-between. Composite materials, various polymers and enamels can be used as the dielectric 18, which shall possess adhesive properties required for joining the electrodes 3, 4. The whole electrodes assembly 19 with the layer of the dielectric 18 has the cylindrical configuration. Dimensions of said electrodes 3, 4 are limited by a typical size of the root canal 1 and 6 of the tooth 2. That's why their length shall not exceed 30 mm and their cross diameter at the butt-end shall be in the range of 0.1-1.5 mm. An extractor kit intended for removal of the metal fragment 5 shall include a set of electrodes assemblies 19 of a number of fixed diameters and lengths enabling the dentist to select the assembly 19 of the maximum diameter, which can still be introduced through the entry 1 into the root canal until the contact with the fragment 5. Besides, said configuration of the electrodes assembly 19 facilitates achievement of the result even if the fragment 5 has an irregular protrusion, which is out-of-line with the axis of the root canal, in direction of the entry 1. It may occur that the fragment 5 touches only one of the electrodes 3, 4 and does not touch the other. Thus the electric circuit remains broken preventing flow of micro-welding current. In this case the dentist turns the electrode assembly 19 with the handle 13 within 180° around its axis trying to achieve the simultaneous contact between both electrodes 3, 4 and the fragment 5. It will be attained when a radius-vector directed from the axis of the canal to the out-of-axis protrusion of the fragment 5 coincides with the orientation of the dielectric strip 18.

The electrodes 3, 4 in the assembly 19 may also have external dielectric coating 20 made from the same material, as dielectric 18, which is shown in FIG. 2. As a material for such dielectric it is expedient to use, for example, Teflon. External dielectric coating 20 does not disturb the flexibility of the electrodes assembly 19 and provides it even more deformation strength during introduction into curved root canal as well as a good electrical and heat insulation of the electrodes from the surrounding tooth tissues. Besides, electrodes with such a coating may be subjected to a multiple wet or dry sterilization.

Figure 3:
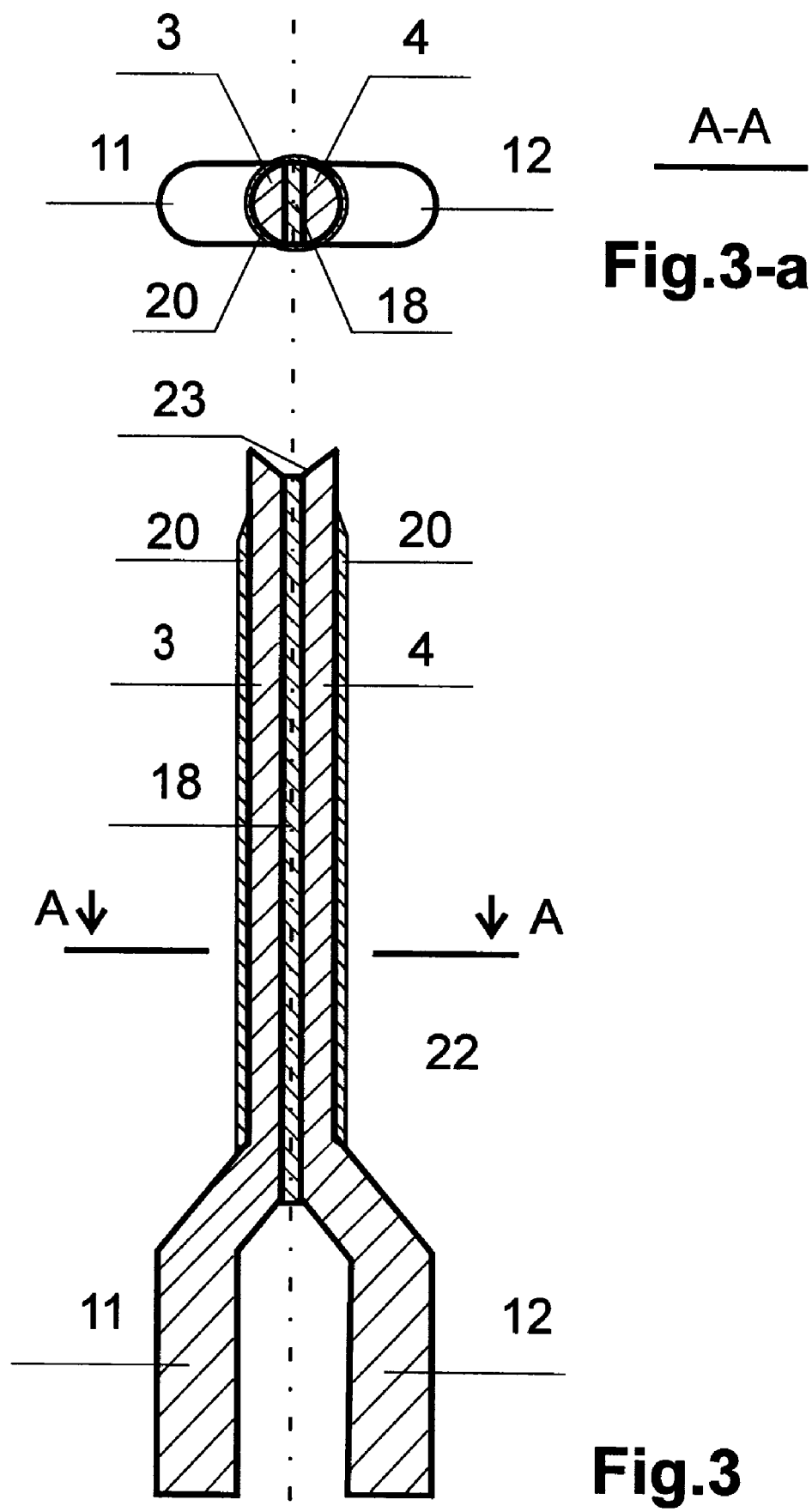
FIG. 3 is a drawing of a cylindrical assembly of insulated electrodes with concave butt-ends used for extraction of the instrument fragment from the root canal.

Since the instrument fragment 5 may be of rather random configuration in the fracture zone, the extractor kit may also include a number of electrode assemblies with a various configuration of the butt-end face, because in order to attain reliable attachment of the fragment 5 to the assembly of electrodes 3, 4 their configurations shall match each other as much as possible, assuring maximum contact area between them. The electrode assembly 19 with the flat butt-end face 21 shown in FIG. 2 is used for attaching to the fragment 5 with a flat butt-end face. Electrode assembly 22 with concave face 23 shown in FIG. 3 is used for attaching the fragment with a convex face. One variant of such butt-end face 23 may be a wedge face shown in FIG. 3.

Figure 4:
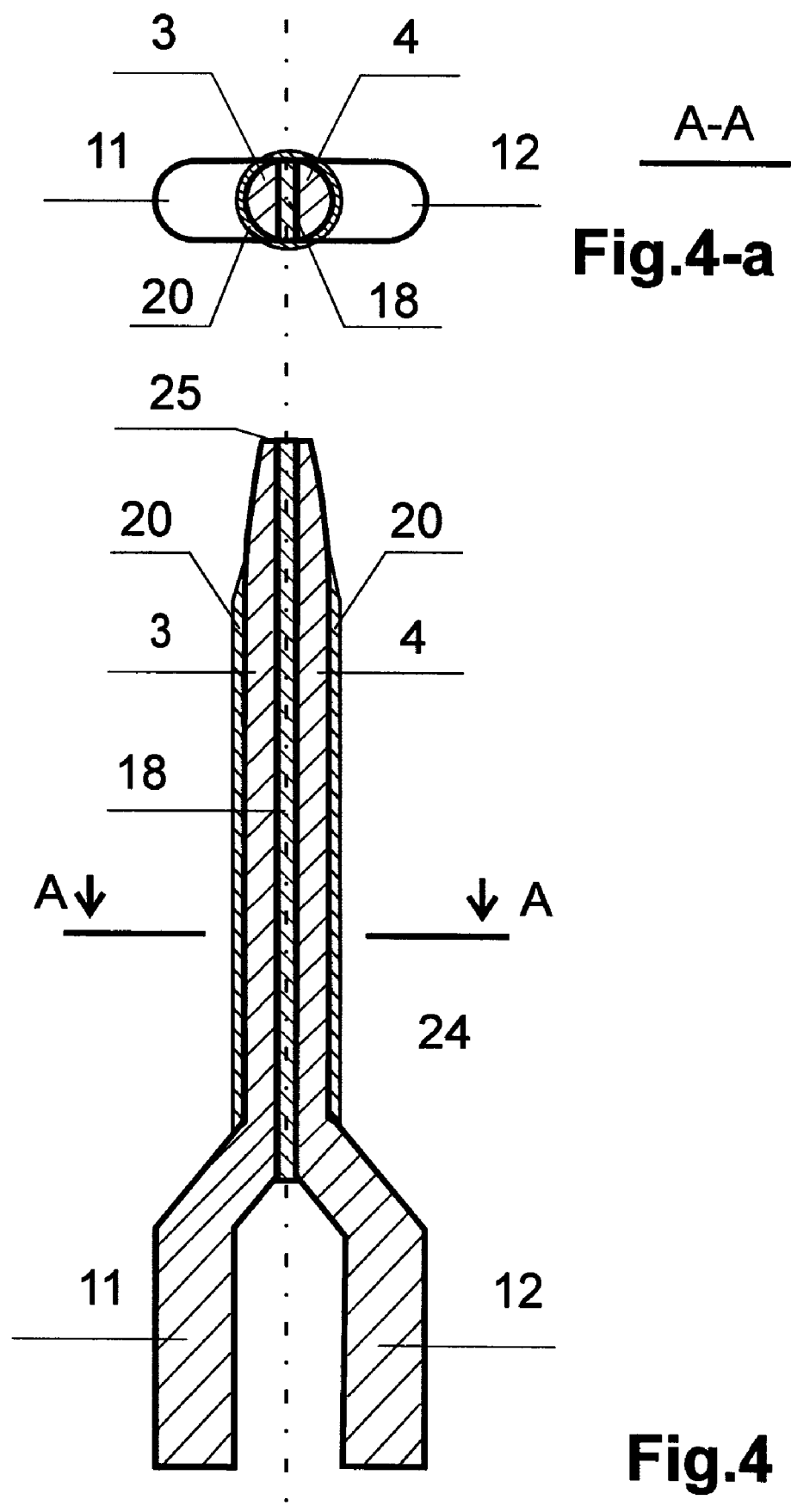
FIG. 4 is a drawing of a cylindrical assembly of insulated electrodes with a tapered tip used for extraction of the instrument fragment from the root canal.

It is also know that the root canal of the tooth is usually of conical form narrowing in the apical (upper) part 6. So, it is expedient to have the assembly 24 with a conic tip shown in FIG. 4 included in said extractor kit. Such configuration of the electrodes 3, 4 ensures maximum utilization of space available in the root canal, increasing durability and reducing electric resistance of the electrodes assembly. Additionally, it provides the alignment of the electrode assembly 24 relative to the axis of the root canal in area 8 as well as preferable contact, in certain cases, between the fragment 5 and the butt-end 25 of the electrodes assembly 24.

It is also expedient to make electrode 3, 4 from the metal or alloy similar to the material of the fragment 5 of the metal instrument. Identical values of electric conductivity, heating capacity and melting temperature of contacting electrodes and fragment provide the best conditions for micro-welding with the lowest possible heat input. Dental instruments used for a treatment of the root canal of the tooth are usually made from various kind of steel including stainless one as well as from Ni—Ti alloy. Therefore, it is recommended to include electrodes made from the relevant materials into said extractor kit.

It is also known that specific electrical resistance of the aforesaid materials used for the dental instruments is much higher than, for example, specific resistance of copper, silver or gold. That's why the supply wires 9, 10 connecting said pulsed current supply source to the electrodes 3, 4 are made from copper wire with a cross section exceeding diameter of the electrodes 3, 4, but with flexibility sufficient for convenient manipulations to be performed by the dentist. For a further reduction of the electric resistance of the circuit and the voltage applied it is possible just before application of dielectric coating 20 to galvanize a metal layer with high electric conductivity (copper, silver, gold) of certain thickness onto the external surface of the electrodes 3, 4 throughout the length, with the exception of the areas surrounding the butt-ends 21, 23, 25.

For said pulsed current supply source various circuits can be used, for example, with DC voltage source commutated to the electrodes 3, 4 for generation of the specified impulse, etc. However, preferred circuit is on the basis of energy storage capacitor shown in FIG. 5. Control of said current supply source is provided by microcontroller 26 based on commercially available single-chip microprocessor with a built-in analogue-to-digital converter (ADC) having several input channels, digital-to-analogue converter (DAC) and digital input/output port. High-current (up to 200 A pulsed) switch, for example, commercially available FET transistor 27 is connected to the control signal output 28 of the microcontroller 26 for commutation of the current through the electrodes 3, 4 and fragment 5. An electrolytic capacitor 29 of no less than 0.1 F value, operating voltage at least 15V and with low internal resistance is connected to the accumulator battery 31 or other source of DC voltage (max 12V) via the switch 30 or current limiting resistor. One of ADC channels in microcontroller 26 is connected to the capacitor 29 via the signal input 32 with appropriate amplifier or voltage divider for the purpose of said capacitor voltage measurement. Microcontroller 26 can also operate the switch 30 via the data output port 33. Via the inputs 32 and 34 it can measure the electric resistance of the circuit passing through the supply wires 9, 10 and the electrodes 3, 4. Display unit 36 is also connected to microcontroller 26 via the port 35, which can indicate the measured resistance value, for instance, on the numerical liquid crystal or light-emitting diodes display and with a beeper of certain sound frequency. Besides, digital input 37 of microcontroller 26 is connected to the "start" pushbutton or to a foot pedal triggering the current impulse via the electrodes 3, 4 and the fragment 5. Power supply source 31 is switched on by the toggle switch 38 and is used to power microcontroller 26 and display unit 36. Integrated DC-DC converter can also be used as a component of the microcontroller 26 to provide a certain DC voltage.

The cycle of extraction of the fragment 5 from the root canal 6 of the tooth 2 is as follows. Microcontroller 26 starts up after actuation of the toggle switch 38. It sets the transistor 27 in the off-state and enables the switch 30 starting a charging of the capacitor 29. When the voltage on the capacitor 29 achieves the pre-determined value, microcontroller 29 disables the switch 30. Then microcontroller 26 enters the mode of periodic measurement of the electric resistance in the circuit segment between the inputs 32 and 34 with indicating this value on display unit 36.

Figure 5:
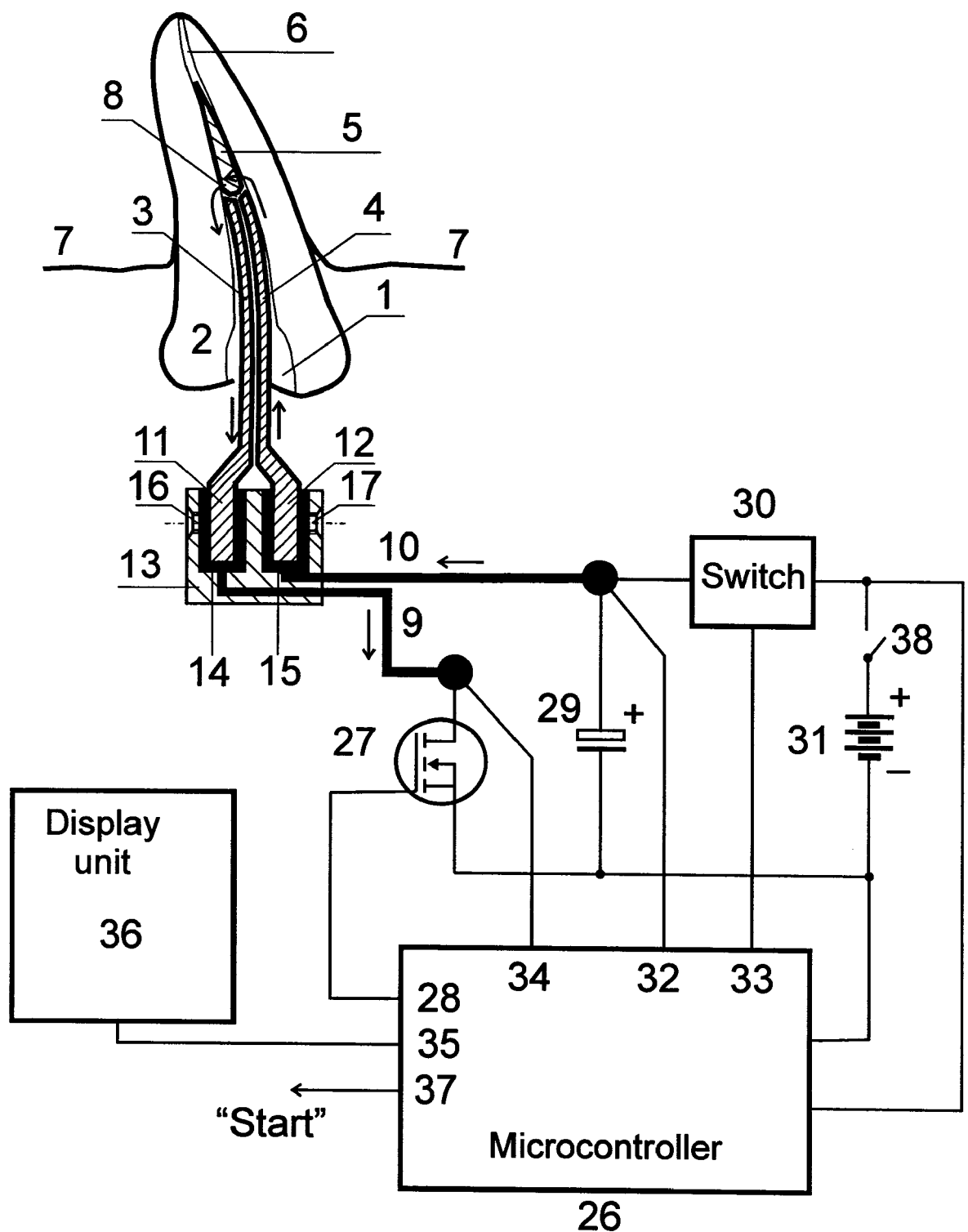
FIG. 5 is a diagram of an electric current supply source connected with two insulated electrodes and ensuring attachment of the fragment to the electrodes by means of the pulsed heating at their contact points and further extraction of the fragment from the root canal together with the electrodes.

When the dentist introduces the electrodes 3, 4 into the entry part 1 of the root canal, display unit 36 indicates high resistance (circuit break) visually and with an audible signal, but when both electrodes 3 and 4 contact the fragment 5, it starts indicating the value of the contact resistance equal to several fractions of Ohm. The dentist can achieve the best contact, i.e. the lowest value of the displayed resistance, by turning and slight pressing on the handle 13. Then the dentist pushes the "start" button or foot pedal and microcontroller 26 activates transistor 27 to on-state so that to pass the electric impulse via the electrodes 3, 4 and the fragment 5 of the circuit, as is shown in FIG. 5 with arrows.

It is known from the bibliographical sources [6] that the quality of the contact micro-welding and, consequently, the strength of the joint between the fragment 5 and the electrodes 3, 4 can be improved by controlling the parameters of the current supply source during the pulse. In particular, pulsed current supply source can be designed to maintain a constant voltage on the circuit segment between said electrodes and said metal fragment to attain the optimal bonding strength between the fragment and the electrodes. It can also be designed to disconnect the voltage timely when the contact resistance is reduced to the optimal level and, consequently, the required bonding strength is achieved. For this purpose microcontroller 26 is measuring the voltage between the electrodes 3, 4 during the current impulse and controls transistor 27 current to maintain the pre-determined voltage value between the electrodes 3, 4. Current through transistor 27 can be controlled both by output voltage of the DAC or by common method of pulse-width modulation under software run of microcontroller 26.

Besides, said pulsed current source can be designed to maintain a stable value (or a pre-determined time diagram) of the current in the circuit between the electrodes 3, 4 and the metal fragment 5 in order to reach a stable temperature in the contact area during the micro-welding pulse. For this purpose, microcontroller 26, while measuring the current between the electrodes 3, 4 during the pulse, controls the current via transistor 27 according to software program by means of the DAC output voltage regulation or by means of pulse-width modulation.

All the possible embodiments of the claimed invention are not restricted to aforementioned partial examples only. These examples do not limit the entire features of the claimed engineering solutions in accordance with the following formula (claims) of the invention.

Common available electronic components are used for the realization of the claimed invention, i.e. field effect transistors as switches, capacitors, microprocessors, etc. The claimed invention can be applied in medicine, specifically, in dentistry during endodontic treatment.

What is claimed is:

1. A method of extracting of a metal fragment from a root canal of a tooth comprising the steps of:
    selecting a first and a second insulated metal electrodes made of a material that is the same or similar in electric conductivity, heating capacity and melting temperature to a material of the metal fragment;
    inserting the first and the second insulated metal electrodes into the root canal and contacting the metal fragment with the electrodes at respective contact points;
    supplying an impulse of an electric current to a circuit formed by the first insulated metal electrode, the metal fragment and the second insulated metal electrode, the current and a duration of the impulse being sufficient for resistance welding of the metal fragment to the first and second insulated metal electrodes at the contact points;
    removing the first and the second electrodes out of the root canal together with the metal fragment welded to the electrodes.

2. The method according to claim 1, further comprising controlling the current and the duration of the impulse to optimize attachment of the metal fragment to the first and the second electrodes during resistance welding and while minimizing a heat impact on tissues surrounding the tooth.

3. The method according to claim 2, wherein a peak value of the impulse is 200 A or less.

4. The method according to claim 2, wherein the duration of the impulse is 0.1 second or less.

5. An extractor for removal of a metal fragment from a root canal of a tooth comprising:
    a first and a second insulated metal electrodes made of a material same or similar in electric conductivity, heating capacity and melting temperature to a material of the metal fragment, the first and the second electrodes having a configuration suitable for insertion into the root canal and for contacting the metal fragment at contact points; and
    a source for supplying an impulse of an electric current to a circuit formed by the first insulated metal electrode, the metal fragment and the second insulated metal electrode, a current and a duration of the impulse being sufficient for resistance welding of the metal fragment to the first and the second insulated metal electrodes at the contact points,
    wherein the source further comprises means for indicating the presence of a contact and a magnitude of electrical resistance between the electrodes and the metal fragments, and means for generating the impulse upon command.

* * * * *